United States Patent [19]

Lee

[11] Patent Number: 5,128,330
[45] Date of Patent: Jul. 7, 1992

[54] OXAZINONE SUBSTITUTED PHOSPHINES
[75] Inventor: Sung J. Lee, Clarks Summit, Pa.
[73] Assignee: Biofor, Ltd., Waverly, Pa.
[21] Appl. No.: 656,505
[22] Filed: Feb. 19, 1991
[51] Int. Cl.$^5$ .................. A61K 31/675; C07D 265/02
[52] U.S. Cl. .......................................... 514/90; 544/3; 544/63
[58] Field of Search ........................ 544/3, 63; 514/90

[56] References Cited
U.S. PATENT DOCUMENTS 4,892,870  1/1990  Lee ........................................ 544/63
4,959,482  9/1990  Lee ....................................... 546/152

Primary Examiner—Mukund J. Shah
Assistant Examiner—Philip I. Datlow
Attorney, Agent, or Firm—Joseph W. Molasky & Assocs.

[57] ABSTRACT

A new class of phosphines in which the phosphorous atom is bonded directly to the carbon of an oxazinone:

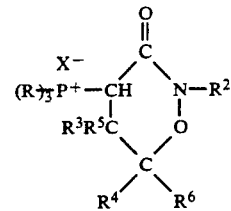

In addition to their anti-inflammatory activity, these phosphines are useful as intermediates in producing compounds where the phosphine is replaced by a benzylidine, compounds which have also been proven useful in the treatment of inflammation and other conditions associated with arthritis.

12 Claims, No Drawings

OXAZINONE SUBSTITUTED PHOSPHINES

This invention relates to a new class of phosphines in which phosphorus is bonded to a heterocyclic nucleus comprised of carbon, oxygen and nitrogen.

More specifically, this invention relates to phosphonium halides in which phosphorus is bonded to the carbon of an isoxzaolidinone, oxazinone or isoxazepinone heterocycle.

The products of this invention exhibit pharmacological activity and, in addition, they are useful as intermediates in preparing the oxaza heterocycles described and claimed in U.S. Pat. No. 4,892,870.

BACKGROUND OF THE INVENTION

The literature contains many references to anti-inflammatory compounds which have in common the di-tert-butyl-4-hydroxyphenyl moiety, also known as "BHT". In U.S. Pat. Nos. 4,892,870 and 4,959,482 I describe two such series of compounds, specifically, oxaza heterocycles in which BHT is a principal component.

Still, there is no definite corrolation between BHT and anti-inflammatory activity so that synthesis and testing provide the only certain means for determining anti-inflammatory effectiveness.

Moreover, the search continues for alternative structures, that is, compounds in which BHT is not present but which, because of their mechanisms and non-steroidal mode of action, can be used to treat the debilitating effects of rheumatoid arthritis and osteoarthritis.

The present invention achieves both goals, that is, it describes agents which are devoid of BHT but which, nevertheless, inhibit mechanisms associated with inflammation.

At the same time, this invention also provides compounds which are useful as intermediates in synthesizing products which possess the BHT structure, products which are particularly active in treating arthritis and conditions associated with that disease. This dual activity is unique to compounds of the present structure and it is totally unexpected based on known activity-structure relationships.

These and other objects will become more readily apparent from the following description.

SUMMARY OF THE INVENTION

This invention provides for a new class of pharmacologically active compounds which have utility as anti-inflammatory agents and which are useful in the treatment of arthritis.

A further object provides for pharmaceutical compositions in which the compounds of this invention are combined with excipients to afford formulations useful in treating diseases characterized by inflammation, pain and/or fever.

In addition to their pharmacological activity the present compounds are also useful as last stage intermediates in producing the benzylidene substituted heterocycles covered by U.S. Pat. No. 4,892,870. These benzylidene compounds have been proven effective as analgesics, immunomodulating agents, anti-inflammatory agents and anti-pyretic agents.

DESCRIPTION OF THE EMBODIMENTS

The products of this invention are compounds having the following general formula:

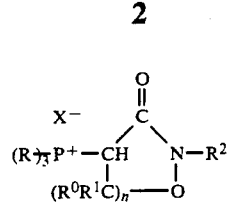

wherein:

R is a member selected from the group consisting of lower alkyl, cycloalkyl and aryl;

$R^0$, $R^1$ and $R^2$ are the same or different and represent a member selected from the group consisting of hydrogen, lower alkyl, lower alkenyl and lower cycloalkyl;

$X^-$ is a halide; and n is an integer having a value of 1-3.

In the foregoing "lower alkyl" refers to straight or branched chain alkyl moieties of from about 1-6 carbon atoms as, for example, methyl, ethyl, n-propyl, isopropyl, n-butyl, isobutyl, n-pentyl, isopentyl, hexyl, isohexyl or the like.

The term "cycloalkyl" refers to mononuclear cycloaliphatic moieties containing from about 3-7 nuclear carbon atoms. Typical of the cycloalkyl moieties intended are, for example, cyclopropyl, cyclobutyl, cyclopentyl, cyclohexyl and cycloheptyl or the like.

The term "aryl" refers to mononuclear and binuclear aromatic moieties as, for example, phenyl, naphthyl or the like.

By "lower alkenyl" is meant mono-unsaturated aliphatic moieties containing from about 2-5 carbon atoms as, for example, vinyl, allyl, isoprenyl, 2-butenyl, 3-methyl-2-butenyl and 3-pentenyl or the like.

The radicals represented by $X^-$ are halides such as fluoride, chloride, bromide and iodide.

A preferred embodiment of this invention resides in those products wherein the heterocyclic nucleus is a 6-membered ring, that is, an oxazinone of the formula:

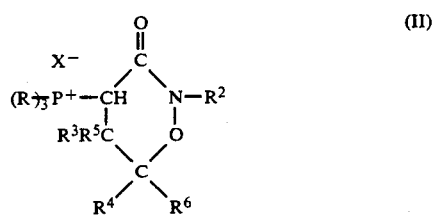

wherein:

R is a member selected from the group consisting of lower alkyl, cycloalkyl and aryl;

$R^2$—$R^6$ are the same or different and represent a member selected from the group consisting of hydrogen, lower alkyl, lower alkenyl and lower cycloalkyl; and $X^-$ is a halide.

These compounds (II) exhibit pronounced anti-inflammatory activity and, therefore, they are uniquely suited for treating the inflammatory effects associated with rheumatoid arthritis and osteoarthritis. Accordingly, they constitute a particularly preferred subgroup of compounds within the scope of this invention.

A second preferred embodiment consists of those products wherein the heterocyclic nucleus is a 5-membered ring, that is, an isoxazolidinone of the formula:

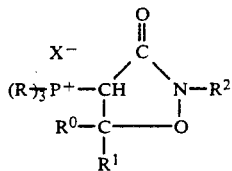

III wherein:

R is a member selected from the group consisting of lower alkyl, cycloalkyl and aryl;

$R^0$ and $R^1$ are the same and different and represent a member selected from the group consisting of hydrogen, lower alkyl, lower alkenyl and lower cycloalkyl; and $X^-$ is a halide.

These compounds (III) also possess anti-inflammatory activity and, therefore, they may be used to alleviate those symptoms to which known anti-inflammatory agents are commonly applied.

Still another embodiment relates to those products in which the heterocyclic nucleus is a 7-membered ring, that is, an isoxazepinone of the formula:

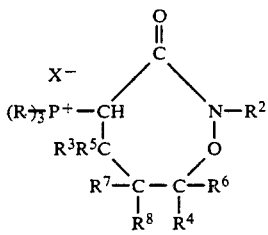

IV wherein:

.R is a member selected from the group consisting of lower alkyl, cycloalkyl and aryl;

$R^2$–$R^8$ are the same or different and represent a member selected from the group consisting of hydrogen, lower alkyl, lower alkenyl and lower cycloalkyl; and $X^-$ is a halide.

These compounds (IV) also exhibit anti-inflammatory activity and they may be used to inhibit the inflammatory effects of rheumatoid arthritis and osteoarthritis.

SYNTHESIS

The products of this invention are obtained by treating a 4-halo precursor with a suitable phosphine:

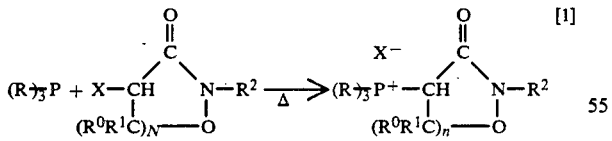

[1]

wherein R, $R^0$, $R^1$, $R^2$, X, $X^-$ and n are as defined above.

The reaction is conducted in a suitably inert solvent with heating over extended periods of up to 20 hours or more. Temperatures in the range of from about 45°–65° C. are preferable but higher temperatures may also be employed.

Suitable solvents include tetrahydrofuran, ethyl ether and other inert mediums but tetrahydrofuran is preferred. The presence of an inert atmosphere enhances product yield.

The product may be purified by washing with additional quantities of tetrahydrofuran or ether but, preferably, tetrahydrofuran, followed by air drying.

The starting materials in this process are either known compounds or they may be obtained by methods known in the art.

The following equation illustrates one such method for preparing precursors in which the heterocycle is a five membered ring, that is, a 4-halo-3-osoxazolidinone; however, the process applies equally to precursors in which the heterocycle is a six and seven membered heterocycle:

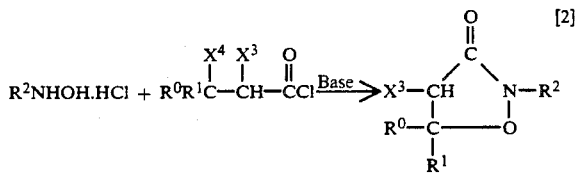

[2]

wherein $X^3$ and $X^4$ are halo such as chloro, bromo, iodo or fluoro and $R^0$, $R^1$ and $R^2$ are as defined above. This process is conducted in the presence of a base such as alkali metal hydroxide or alkali metal carbonate as, for example, sodium hydroxide and potassium carbonate.

Those precursors in which the heterocyclic nucleus is a six-membered ring and seven-membered ring are prepared in a manner similar to that shown above except that 2,4-dihaloalkanoyl chloride ([3], below) and 2,5-dihaloalkanoyl chloride ([4], below) are substituted for the 2,3-dihaloalkanoyl chloride of equation [2] above:

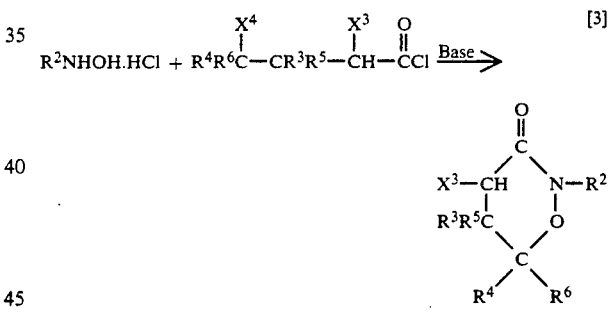

[3]

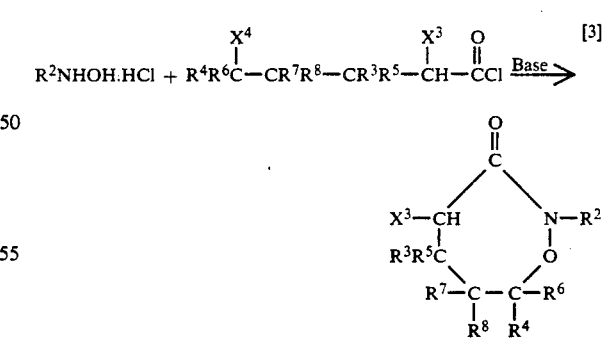

[3]

wherein $R^2$—$R^8$, $X^3$ and $X^4$ are as defined above.

In addition to their pharmacological activity the products of this invention have utility as intermediates in preparing the pharmacologically active products described and claimed in U.S. Pat. No. 4,892,870. According to this procedure the present compounds are first treated with a 3,5-di-tert-butyl-4-hydroxybenzaldehyde in the presence of a strong base such as triethylamine with heating and the resulting mixture is then cooled, washed and dried to afford the benzylidene product:

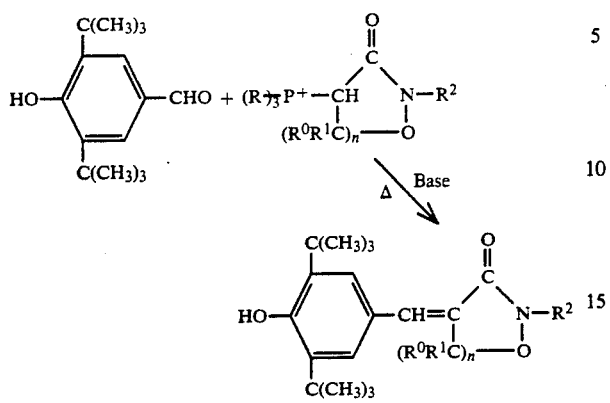

Principal among these intermediates is the (dihydro-N-methyl-2H-1,2-oxazin-3(4H)-oxo-4-yl)triphenylphosphonium bromide of Example 1, a compound which, upon treatment with base at elevated temperatures, yields dihydro-4-(3,5-di-tert-butyl-4-hydroxybenzylidene)-N-methyl-2H-1,2-oxazin-3(4H)-one, a product which is uniquely suitable for treating the inflammatory effects of rheumatoid arthritis and osteoarthritis.

PHARMACOLOGY

The compounds (I) of this invention are effective in the treatment of inflammation, pain and/or fever in arthritic test systems; moreover, they exhibit this effectiveness over extended periods with little or no evidence of toxicity. This effectiveness is particularly evident in those compounds (I) wherein the phosphene moiety is bonded to a six membered heterocyclic ring, that is, the oxazinone heterocycle:

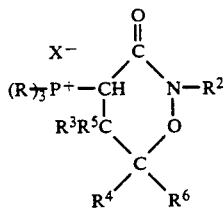

II wherein:

R, $R^2$-$R^6$ and $X^-$ are as defined above; including the non-toxic pharmacological acceptable salts thereof. These compounds (II) combine surprisingly good anti-inflammatory activity with very favorable therapeutic indices and they have the ability to maintain this effectiveness over prolonged periods at low dosage levels.

The assays for the present compounds (I) and their modes of administration are based on known test systems and these are described hereinbelow.

Assay: The pharmacological properties of the present compounds (I) were determined by assay procedures which measured their ability to evoke a characteristic response in test animals.

Anti-Inflammatory: This activity was evaluated using a modification of the carrageenan-induced paw edema test described by C. A. Winter et al in Proc. Soc. Exp. Biol. and Med.,III: page 544 (1962). This assay measures the ability of the test compound to antagonize local edema, a characteristic of the inflammatory response.

Formulation: The products (I) of this invention may be employed as the active ingredient in a variety of pharmaceutical compositions in admixture with a pharmaceutically acceptable solid or liquid diluent or carrier. Pharmaceutically acceptable diluents or carriers include any nontoxic substance which, when mixed with a product of this invention, renders it more suitable for administration either orally, intravenously or intermuscularly. Typical of the diluents or carriers intended are solid, liquid and semi-solid diluents and carriers such as paraffins, vegetable oils, mannitol, sucrose, glucose or sterile liquids such as water, saline, glycols and oils of a petroleum, animal, vegetable or synthetic origin as, for example, peanut oil, mineral oil and sesame oil. Moreover, the composition may be enhanced by including other useful ingredients such as stabilizers, binders, antioxidants, preservatives, lubricators, suspending agents, viscosity aids or flavoring agents and the like.

The compositions may also include one or more other ingredients having pharmacological activities of their own so as to provide a broad spectrum of activity. For example, in the treatment of inflammation one common complication is the occurrence of edema, a condition which may be alleviated by combining a compound of this invention with an appropriate diuretic and/or anorectic. The nature and quantity of these added ingredients will depend largely upon the malady to be treated and the weight of the patient and, therefore, the precise nature of the composition must be left to the practitioner to determine.

Dosage: The dose to be administered depends to a large extent upon the condition being treated and the weight of the host; however, a general daily dosage may consist of from about 0.1 mg to 500 mg of active ingredient per kilogram of body weight which may be administered in a single dose or multiple doses. A total preferred daily dose lies in the range of from about 0.25 mg to 100 mg of active ingredient per kilogram of body weight.

Unit Dosage Forms: The compositions of this invention may be administered parenterally or orally in solid and liquid oral unit dosage form as, for example, in the form of tablets, capsules, powders, suspensions, solutions, syrups, sustained release preparations and fluid injectable forms such as sterile solutions and suspensions. The term "unit dosage form" as used in this specification refers to physically discrete units which are administered in single or multiple dosages, each unit containing a predetermined quantity of active ingredient in combination with the required diluent, carrier or vehicle.

Solid Tablets: Hard tablets are prepared by combining the active ingredient, suitably comminuted, with a diluent such as starch, sucrose, kaolin or calcium phosphate and a lubricant. Optionally, the compositions may contain stabilizers, anti-oxidants, preservatives, suspending agents, viscosity aids, flavoring agents and the like. The composition is pressed into tablets and a protective coating of shellac, wax, sugar or polymeric material is added. If desired, dyes can also be included to provide a color-code means for distinguishing between different dosages.

Chewable Tablets: This unit dosage form is prepared by combining the active ingredient with a pharmaceutically acceptable orally ingestible solid carrier and a gum base. If desired, the composition may also contain flavors, binders, lubricants and other excipients.

Soft Capsule: Soft gelatin capsules are prepared by dissolving the active ingredient in a pharmaceutically acceptable oil such as peanut oil, sesame oil or corn oil together with glycerine and water.

Hard Capsule: Hard gelatin capsules may be prepared by mixing the active ingredient with lactose and magnesium stearate and placing the mixture in a No. 3 gelatin capsule. If desired, a glidant such as colloidal silica may also be added to improve flow properties and a distintegrating or solubilizing agent may be included to improve the availability of the medicament upon injection.

Liquids: Syrups, elixirs and suspensions can be prepared in unit dosage from so that the compositions can be administered by the teaspoonful. Syrups are prepared by dissolving the compounds in a suitably flavored aqueous sucrose solution, whereas, elixirs are prepared by combining the active ingredient with non-toxic alcoholic vehicles. Suspensions are obtained by mixing a dry powder containing the active ingredient in water with a minor amount of a suspending agent, a flavoring agent, a sweetener such as sugar, and a preservative if necessary.

Parenteral: Unit dosage forms suitable for parenteral administration are prepared by suspending or dissolving a measured amount of the active ingredient in a non-toxic liquid vehicle suitable for injection such as an aqueous or oleaginous medium and sterilizing the resulting mixture.

Alternatively, a measured amount of the active ingredient may be placed in a vial as a discrete entity and the vial and its contents can be sterilized and sealed. If desired, an accompanying vial containing an appropriate vehicle for admixture with said active ingredient can also be provided so that the contents of both vials can be combined and mixed for administration purposes immediately prior to use.

Topical: Powders and other solid unit dosage forms can be formulated by combining an active ingredient of this invention with a suitable carrier such as talc, bentonite, silicic acid, polyamide powder, animal and vegetable fats, wax, paraffins, starch, tragacanth, cellulose deriviatives, polyethylene glycols, silicones and zinc oxide or mixtures thereof.

Liquid and semi-liquid formulations on the other hand can be prepared in the form of suspensions, solutions, ointments, pastes, creams and gels by combining an active ingredient with such carriers as polyethylene glycol, vegetable and mineral oils or alcohols such as isopropanol and the like.

In addition to the aforementioned carriers the formulations can also include such other excipients as emulsifiers, preservatives, colorants, perfumes and the like.

The pH of the formulation should approximate values suitable for application to normal skin, that is, the formulation should possess a pH range of from about 6–6.5 and buffers may be added to the compositions to achieve and maintain this pH range. Typical of a buffer which may be used for this purpose is, for example, an aqueous mixture of acetic acid and sodium lactate. The water employed in preparing this buffer should be distilled or demineralised to ensure dermatological acceptability.

This invention will now be described by reference to precise embodiments.

EXAMPLE 1

(DIHYDRO-N-METHYL-2H-1,2-OXAZIN-3(4H)-OXO-4-YL)TRIPHENYLPHOSPHONIUM BROMIDE

Step A:
Dihydro-4-Bromo-N-Methyl-2H-1,2-Oxazin-3(4H)-One

To a stirred mixture of 510 g (6.1 mol) of N-methylhydroxylamine hydrochloride dissolved in 750 ml of distilled water and 469 g (6 mol) of 51.2% sodium hydroxide solution placed in a 22 liter round bottom flask cooled by an icesalt bath ($-5°$ C.) there was added 3 ml of 0.04% phenol red solution, 50 g (0.22 mol) of benzyltriethylammonium chloride and 12 liters of methylene chloride pre-cooled to $-7°$ C. The resulting mixture was pink in color. A solution containing 1590 g (6 mol) of 2,4-dibromobutyrylchloride diluted to 2 liters with methylene chloride was placed in an addition funnel and 470 g (6 mol) of a 51.2% sodium hydroxide solution was placed in a second addition funnel. The addition of 2,4-dibromobutyrylchloride solution to the mixture resulted in a light yellow color and after the first 25 ml had been added the sodium hydroxide addition was begun. The acid chloride was added at a rate of 7 ml/minute and sodium hydroxide was added at a rate of 2 ml/minute. The yellow color of the reaction mixture was maintained and the reaction mixture was continuously stirred at high speed while maintaining the temperature below 5° C. The entire addition required approximately 5 hours.

Sodium carbonate (53 g, 5 mol) was then added and the reaction mixture assumed a pink color which was maintained for 5 minutes. At 20 minute intervals, 53 g portions of anhydrous sodium carbonate were added until a total of 318 g (3 mol) had been added. The temperature was maintained below 5° C. and after ten hours an additional 318 g (3 mol) of sodium carbonate was added in 53 g portions followed by the addition of 1 liter of water. The reaction mixture was brought to room temperature and stirred for an additional 64 hours. Two liters of 10% sulfuric acid were added, followed by the addition of 6 liters of water. The organic phase was separated and the aqueous phase extracted with 4 liters of methylene chloride. The combined organic phase was dried over anhydrous sodium sulfate and passed through a short column of silica gel (1.5 kg) with ethyl acetate. The resulting crude product was then chromatographed on silica gel to yield 483 g (2.48 mol) of syrupy dihydro-4-bromo-N-methyl-2H-1,2-oxazin-3(4H)-one.

Step B:
(Dihydro-N-Methyl-2H-1,2-Oxazin-3(4H)-Oxo-4-yl)-triphenylphosphonium Bromide A solution containing 5.4 g (28 mmol) of dihydro-4-bromo-N-methyl-2H-1,2-oxazin-3(4H)-one, 7.5 g (29 mmol) of triphenylphosphine and 15 ml of tetrahydrofuran was heated at 55° C. with stirring under an atmosphere of nitrogen for 17 hours. The reaction mixture was cooled to room temperature and filtered. The collected solid was washed successively with tetrahydrofuran and ether and air dried to yield 4.8 g (11 mmol) of (dihydro-N-methyl-2H-1,2-oxazin-3(4H)-oxo-4-yl)triphenylphosphonium bromide, mp 206° C.

$^1$HNMR(CDCl$_3$)γ2.12(m,1H), 2.92(m,1H), 3.09(s,3H), 4.17(m,1H), 4.66(m,1H), 7.18(m,1H), 7.61-8.05(m,15H).

IR(KBr)cm$^{-1}$ 3405(broad,w), 2770(w), 1653(w), 1626(s), 1482(w), 1437(ms), 1180(w), 1110(m), 1032(w), 746(mw).

By following the procedure of Example 1, Steps A and B, other phosphonium halides may be obtained. The following equation illustrates this procedure and with Table I, infra, it further illustrates the starting materials of this process and the products obtained thereby:

R$^2$NHOH.HCl +

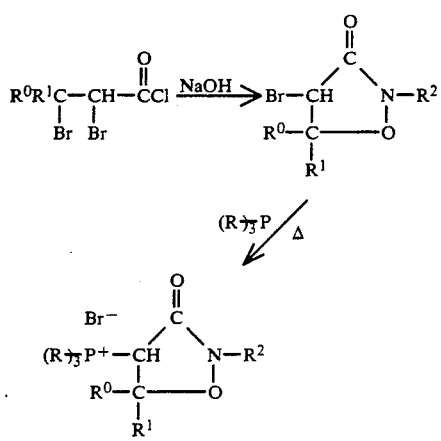

TABLE I

| Ex. | R | R$^0$ | R$^1$ | R$^2$ |
|---|---|---|---|---|
| 2 | —C$_2$H$_5$ | H | H | —CH$_3$ |
| 3 | —CH$_3$ | H | —CH$_2$CH=CH$_2$ | —CH$_3$ |
| 4 | ⌬ (phenyl) | —CH$_3$ | —CH$_3$ | H |
| 5 | ⌬ (phenyl) | H | H | —CH$_3$ |

TABLE I-continued

| Ex. | R | R$^0$ | R$^1$ | R$^2$ |
|---|---|---|---|---|
| 6 | —CH$_3$ | H | —CH(CH$_2$)(CH$_2$) cyclopropyl | H |
| 7 | thiacyclohexyl (S) | H | H | —C$_2$H$_5$ |
| 8 | —CH$_2$C$_2$H$_5$ | H | H | —CH$_2$CH=CH$_2$ |
| 9 | —CH$_3$ | H | H | —CH(CH$_2$)(CH$_2$) cyclopropyl |

The preceding equation and Table describe products in which the heterocyclic moiety is a 5-membered ring, that is, a 1,2-isoxazolidin-3(4H)-oxo-4-yl radical. The 6-membered heterocycles may be prepared in a similar manner by substituting for the 2,3-dibromoalkanoyl chloride therein shown the next higher homolog, that is, a 2,4-dibromoalkanoyl chloride. The following equation and Table illustrate this process and the products obtained thereby:

R$^2$NHOH.HCl +

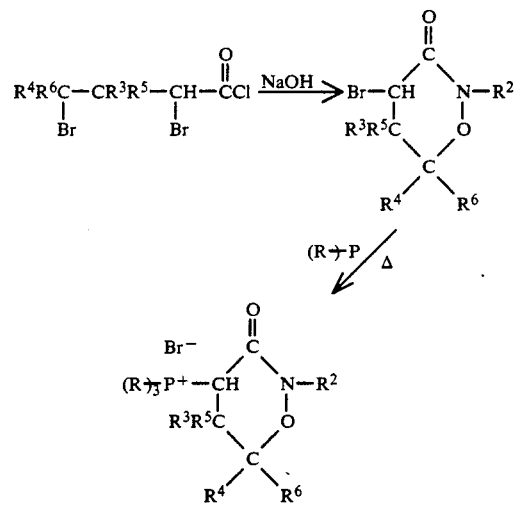

TABLE II

| Ex. | R | R$^2$ | R$^3$ | R$^4$ | R$^5$ | R$^6$ |
|---|---|---|---|---|---|---|
| 10 | —C$_2$H$_5$ | —C$_2$H$_5$ | —CH$_3$ | H | —CH$_3$ | —CH$_3$ |
| 11 | —CH$_3$ | —CH$_3$ | H | —CH$_2$CH=CH$_2$ | H | H |
| 12 | ⌬ (phenyl) | —C$_2$H$_5$ | —CH$_3$ | H | —CH$_3$ | —CH$_3$ |
| 13 | —CH$_3$ | H | —CH(CH$_2$)(CH$_2$) cyclopropyl | H | H | H |
| 14 | —CH$_3$ | —CH$_3$ | H | H | H | H |

TABLE II-continued

| Ex. | R | $R^2$ | $R^3$ | $R^4$ | $R^5$ | $R^6$ |
|---|---|---|---|---|---|---|
| 15 | phenyl | —CH₃ | —CH₃ | H | —CH₃ | H |
| 16 | thiacyclohexyl (S) | —CH₃ | H | H | H | —CH₃ |
| 17 | phenyl | —CH₃ | H | —CH₃ | —CH₃ | H |

The 3-isoxazepinone analogs are obtained by substituting a 2,5-dibromoalkanoyl chloride for the 2,4-dibromoalkanoyl chloride of the preceding equation and otherwise following the procedure therein shown. This procedure and the resulting products are illustrated by the following equation and Table:

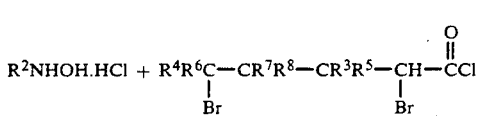

$$R^2NHOH \cdot HCl + R^4R^6C-CR^7R^8-CR^3R^5-CH-CCl$$
(with Br substituents, $\xrightarrow{NaOH}$)

-continued (phosphonium bromide intermediate structure with $R^2$, $R^3R^5$, $R^7$, $R^8$, $R^4$, $R^6$)

TABLE III

| Ex. | R | $R^2$ | $R^3$ | $R^4$ | $R^5$ | $R^6$ | $R^7$ | $R^8$ |
|---|---|---|---|---|---|---|---|---|
| 18 | —C₂H₅ | —CH₃ | —CH₃ | H | —CH₃ | H | H | —CH₃ |
| 19 | —CH₃ | —C₂H₅ | H | H | H | H | H | H |
| 20 | —C₂H₅ | H | —C₂H₅ | H | H | —CH₃ | H | H |
| 21 | phenyl | H | —CH₃ | —CH₃ | H | H | H | H |
| 22 | phenyl | —CH₃ | H | H | H | H | H | —CH₃ |
| 23 | —CH₃ | —CH₃ | H | H | —CH₃ | H | —CH₃ | —CH₃ |

The following example illustrates a method by which the products of this invention may be used as intermediates to synthesize the pharmacologically active products of U.S. Pat. No. 4,892,870.

EXAMPLE 24

DIHYDRO-4-(3,5-DI-TERT-BUTYL-4-HYDROXYBENZYLIDENE)-N-METHYL-2H-1,2-OXAZIN-3(4H)-ONE (Dihydro-N-methyl-2H-1, 2-oxazin-3(4H)-oxo-4-yl)-triphenylphosphonium bromide (323 g, 0.71 mol), 160 g (683 mmols) of 3,5-di-tert-butyl-4-hydroxybenzaldehyde, 200 ml of triethylamine (1.43 mol) and 3 liters of absolute ethanol were stirred for 18 hours at room temperature. The reaction mixture was then heated to 42° C., stirred for an additional hour and concentrated in vacuo to a volume of 1.5 liters. Upon cooling to room temperature the concentrated mixture was filtered and washed successively with a 10% ethanol-hexane mixture and water. The resulting product was air dried to afford 140 g of dihydro-4-(3,5-di-tert-butyl-4-hydroxybenzylidene)-N-methyl-2H-1,2-oxazin-3(4H)-one, an antiinflammatory agent described and claimed in U.S. Pat. No. 4,892,870.

To increase product yield the filtrate obtained in the foregoing process was concentrated, filtered, diluted with methylene chloride, washed with dilute hydrochloric acid, dried over anhydrous sodium sulfate, concentrated again and chromatographed. In this way, there was obtained an additional 20 g of dihydro-4-(3,5-di-tert-butyl-4-hydroxybenzylidene)-N-methyl-2H-1,2-oxazin-3(4H)-one.

The following embodiments illustrate the preparation of typical unit dosage forms, it being understood that other active ingredients, excipients and vehicles may be substituted therefor to provide a variety of other formulations suitable for oral and/or pharenteral administration.

EXAMPLE 25

Dry Filled Capsule

A dry filled capsule is prepared by mixing the following ingredients:

| Ingredient | Mg. Per Capsule |
| --- | --- |
| (Dihydro-N-methyl-2H-1,2-oxazin-3(4H)-oxo-4-yl)triphenylphosphonium bromide | 500 |
| Lactose | 225 |
| Magnesium Stearate | 10 |

The (dihydro-N-methyl-2H-1,2-oxazin-3(4H)-oxo-4-yl)-triphenylphosphonium bromide is reduced to a No. 60 powder. Lactose and magnesium stearate are passed through a No. 60 bolting cloth onto the powder and the combined ingredients are admixed for ten minutes and filled into a suitable gelatin capsule.

EXAMPLE 26

Compressed Tablet

A compressed tablet suitable for swallowing is prepared by mixing the following ingredients:

| Ingredients | Mg. Per Tablet |
| --- | --- |
| (Dihydro-N-methyl-2H-1,2-oxazin-3(4H)-oxo-4-yl)triphenylphosphonium bromide | 200 |
| Lactose (U.S. No. 80 powder) | 100 |
| Cornstarch | 50 |
| Magnesium Stearate | 5 |

The (dihydro-N-methyl-2H-1,2-oxazin-3(4H)-oxo-4-yl)-triphenylphosphonium bromide and lactose are mixed thoroughly and granulated with starch paste. The granulated composition is passed through a No. 14 screen while still moist and dried at 45° C. in an oven. When drying is complete the dried material is passed several times through a No. 14 screen and cornstarch is added by passage through a No. 90 bolting cloth. This combination of ingredients is blended and magnesium stearate is added by passage through a No. 60 bolting cloth. The resulting mixture then is blended to a homogeneous mass and pressed into tablets weighing 355 mg per unit.

EXAMPLE 27

Oral Liquid

A liquid formulation suitable for oral administration is prepared from the following ingredients:

| Ingredients | G. Ml Per Dose |
| --- | --- |
| (Dihydro-N-methyl-2H-1,2-oxazin-3(4H)-oxo-4-yl)triphenylphosphonium bromide | 150 g |
| Sucrose | 200 g |
| Glucose | 100 g |
| Citric Acid | 13 g |
| Sodium Benzoate | 1.0 g |
| Concentrated Orange Oil | 0.2 ml |
| Purified Water, U.S.P. (Sufficient to produce | 1000 ml) |

Sucrose and glucose are dissolved in 400 ml of water with heating following which the solution is cooled and citric acid, sodium benzoate and concentrated orange oil are added. The solution is brought to a volume of about 900 ml by the addition of water and (dihydro-N-methyl-2H-1,2-oxazin-3(4H)-oxo-4-yl)-triphenylphosphonium bromide is added. The solution is then filtered and brought to a volume of 1000 ml to provide a liquid suitable for oral adminsitration.

EXAMPLE 28

ANTIINFLAMMATORY ACTIVITY

Acute antiinflammatory activity was evaluated using the carrageenan-induced paw edema test described by C. A. Winter, et al in Proc. Soc. Exp. Biol. and Med., III, page 544 (1962).

Male Sprague-Dawley rats were divided into groups of six rats each. Paw volumes were determined by mercury displacement and all rats were dosed with the test compounds suspended in 0.25% methylcellulose. One hour after dosing with the test compounds, the left hind paws were injected with a 0.1 ml carrageenan solution (1% in distilled water, sterilized) intraplantarly. Three hours after carrageenan injection the volume of the injected paws was redetermined. Group means were also determined and the drug effect was calculated as percent inhibition of the hind paw edema according to the following equation:

$$\% \text{ Inhibition} = \frac{\text{(Mean Control Edema} - \text{Mean Expt. Edema)}}{\text{Mean Control Edema}} \times 100$$

The results of this study are set forth below. The test compounds were the product of Example 1, that is, (dihydro-N-methyl-2H-1,2-oxazin-3(4H)-oxo-4-yl)triphenylphosphonium bromide, and a known antiinflammatory, Aspirin.

TABLE IV

| Compound | Dosage | % Inhibition |
| --- | --- | --- |
| Example 1 | 100 mg/kg | 62 |
| Aspirin | 100 mg | 50 |
| Control | — | 0 |

What is claimed is:
1. A compound of the formula:

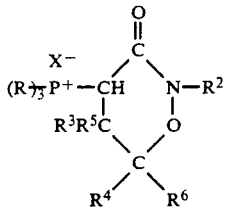

wherein:
R is a member selected from the group consisting of lower alkyl, mononuclear cycloalkyl of from about 3–7 carbon atoms, mononuclear aryl and binuclear aryl;

$R^2$—$R^6$ are the same or different and represent a member selected from the group consisting of hydrogen, lower alkyl, lower alkenyl and lower cycloalkyl; and $X^-$ is a halide.

2. A compound according to claim 1 wherein R is phenyl.

3. A compound according to claim 1 wherein $R^2$ is lower alkyl and $R^3$–$R^6$ are hydrogen.

4. A compound according to claim 3 wherein $X^-$ is bromide.

5. (Dihydro-N-methyl-2H-1,2-oxazin-3(4H)-oxo-4-yl)-triphenylphosphonium bromide.

6. A pharmaceutical composition wherein the active ingredient is a compound of the formula:

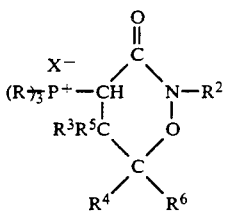

wherein:
R is a member selected from the group consisting of lower alkyl, mononuclear cycloalkyl of from about 3–7 carbon atoms, mononuclear aryl and binuclear aryl;

$R^2$–$R^6$ are the same or different and represent a member selected from the group consisting of hydrogen, lower alkyl, lower alkenyl and lower cycloalkyl; and $X^-$ is a halide; and a pharmaceutically acceptable carrier.

7. A pharmaceutical composition according to claim 6 wherein the active ingredient is a compound in which R is phenyl.

8. A pharmaceutical composition according to claim 7 wherein the active ingredient is (dihydro-N-methyl-2H-1,2-oxazin-3(4H)-oxo-4-yl)triphenylphosphonium bromide.

9. A method for treating inflammation in a mammal which comprises administering a safe and effective amount of a compound having the formula:

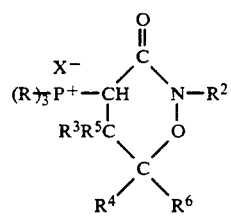

wherein:
R is a member selected from the group consisting of lower alkyl, mononuclear cycloalkyl of from about 3–7 carbon atoms, mononuclear aryl and binuclear aryl;

$R^2$–$R^6$ are the same or different and represent a member selected from the group consisting of hydrogen, lower alkyl, lower alkenyl and lower cycloalkyl; and $X^-$ is a halide.

10. A method according to claim 9 wherein the active ingredient is (dihydro-N-methyl-2H-1,2oxazin-3(4H)-oxo-4-yl)-triphenylphosphonium bromide.

11. A method according to claim 9 wherein R is phenyl.

12. The compound according to claim 1 wherein R is phenyl.

* * * * *